(12) United States Patent
Pedrazzini

(10) Patent No.: US 10,041,965 B2
(45) Date of Patent: Aug. 7, 2018

(54) MODIFIED DEVICE FOR TRANSPORTING A CONTAINER OF BIOLOGICAL PRODUCTS IN A LABORATORY AUTOMATION SYSTEM

(71) Applicant: INPECO HOLDING LTD., Qormi, QRM (MT)

(72) Inventor: Gianandrea Pedrazzini, Paradiso (CH)

(73) Assignee: INPECO HOLDING LTD., Qormi, QRM (MT)

( * ) Notice: Subject to any disclaimer, the term of this patent is extended or adjusted under 35 U.S.C. 154(b) by 34 days.

(21) Appl. No.: 15/302,286

(22) PCT Filed: Apr. 7, 2015

(86) PCT No.: PCT/EP2015/057436
§ 371 (c)(1),
(2) Date: Oct. 6, 2016

(87) PCT Pub. No.: WO2015/155147
PCT Pub. Date: Oct. 15, 2015

(65) Prior Publication Data
US 2017/0030939 A1    Feb. 2, 2017

(30) Foreign Application Priority Data
Apr. 9, 2014 (IT) .............................. MI2014A0664

(51) Int. Cl.
*B01L 9/06* (2006.01)
*G01N 35/02* (2006.01)
*G01N 35/04* (2006.01)

(52) U.S. Cl.
CPC .............. *G01N 35/026* (2013.01); *B01L 9/06* (2013.01); *G01N 35/04* (2013.01); *B01L 2200/023* (2013.01); *B01L 2200/025* (2013.01); *B01L 2300/022* (2013.01)

(58) Field of Classification Search
None
See application file for complete search history.

(56) References Cited

U.S. PATENT DOCUMENTS

| 5,941,366 | A | 8/1999 | Quinlan et al. | |
|---|---|---|---|---|
| 8,147,778 | B2 | 4/2012 | Pedrazzini | |
| 9,211,543 | B2 * | 12/2015 | Ohga | B01L 9/06 |
| 2005/0037502 | A1 | 2/2005 | Miller | |
| 2005/0180896 | A1 * | 8/2005 | Itoh | B01L 9/06 |
| | | | | 422/400 |
| 2006/0222573 | A1 * | 10/2006 | Itoh | B01L 9/06 |
| | | | | 422/400 |
| 2010/0226828 | A1 * | 9/2010 | Itoh | B01L 9/06 |
| | | | | 422/562 |
| 2014/0093438 | A1 * | 4/2014 | Yanez | B01L 9/06 |
| | | | | 422/561 |

OTHER PUBLICATIONS

International Search Report, dated Apr. 28, 2015 (2 pages).

* cited by examiner

*Primary Examiner* — Paul S Hyun
(74) *Attorney, Agent, or Firm* — Jacobson Holman, PLLC.

(57) ABSTRACT

Described is a carrier device for a single container of biological products or single test tube, comprising a base with a cavity, and a closing element. The base has a central pin with a cavity in which an RFID transponder is accommodated, is rotationally coupled to a toothed rotor, and further comprises four coupling holes, obtained in four cylinders projecting upward and having vertical axes, in which pins of four vertical gripping fingers are inserted.

1 Claim, 2 Drawing Sheets

MODIFIED DEVICE FOR TRANSPORTING A CONTAINER OF BIOLOGICAL PRODUCTS IN A LABORATORY AUTOMATION SYSTEM

BACKGROUND OF THE INVENTION

The present invention relates to a modified device for transporting a container of biological products in a laboratory automation system.

Within the scope of transporting biological samples inside analysis laboratories, carrier devices have now been used for some time which are capable of accommodating specific containers of biological products, typically single test tubes, which in turn accommodate therein the aforesaid biological sample (blood, urine or other).

Such carrier devices for single test tubes travel along a conveyor belt of an automation system to be transferred from one point to another of the laboratory, and therefore allow the test tubes accommodated therein to interface with different pre- or post-analysis modules, and also with the true analysis modules of the sample, present in the laboratory.

However, the hold of such carrier devices is not always perfect, that is the capacity to securely hold the test tubes therein accommodated, in response to different types of stresses to which the test tubes may be subjected, and also to keep the precisely vertical position thereof.

Such a risk is particularly significant both during transport between the various modules present in the laboratory and especially when the test tube is inserted into/removed from the carrier device.

U.S. Pat. No. 8,147,778 of this Applicant describes a carrier device for a single container of biological products or single test tube comprising a base with a cavity, and a closing element.

Said base has a central pin with a cavity in which an RFID transponder is accommodated, is rotationally coupled to a rotor having toothed portions or a single ring gear, and further comprises coupling holes in which pins of four vertical gripping fingers are inserted.

Each of said fingers has, in turn, a toothed portion which engages a toothed portion of the rotor, as well as pins which engage coupling holes of the closing element.

The device described in U.S. Pat. No. 8,147,778 further comprises four spiral springs—one for each finger—having horizontal axis, which are adapted to rotationally connect the fingers with the base. Said springs have ring-shaped coupling ends adapted to embrace pins which are integral with the fingers and the base, respectively.

Disadvantageously, the assembly of the device is difficult, in particular the installation of the springs.

Equally disadvantageously, the springs are never perfectly equal to one another, thus determining a non-uniform holding stress of the four fingers on the test tube, which therefore may tilt.

Said disadvantages increase when test tubes of different sizes are used for the same carrier device.

US-2005/0037502 describes a carrier device for a single test tube with a rotor to which gripping fingers are coupled. A spring for holding the test tube is provided about said rotor.

BRIEF SUMMARY OF THE INVENTION

It is the object of the present invention to make an improved carrier device for a single test tube, which ensures an always increasing safety in holding the test tube during all types of operation to which it may be subjected, thus avoiding it from being improperly tilted, in particular during the insertion or removal operations of the test tube into/from the carrier device and in light of subsequent operations to be performed on the biological sample therein contained.

It is a further object of the present invention to make a carrier device that is simpler to assemble and less subject to wear.

BRIEF DESCRIPTION OF THE DRAWINGS

These and other objects are achieved by a carrier device as described in claim 1.

These and other features of the present invention will become increasingly apparent from the following detailed description of one of its non-limiting embodiments, disclosed in the accompanying drawings, in which.

Figure 1:
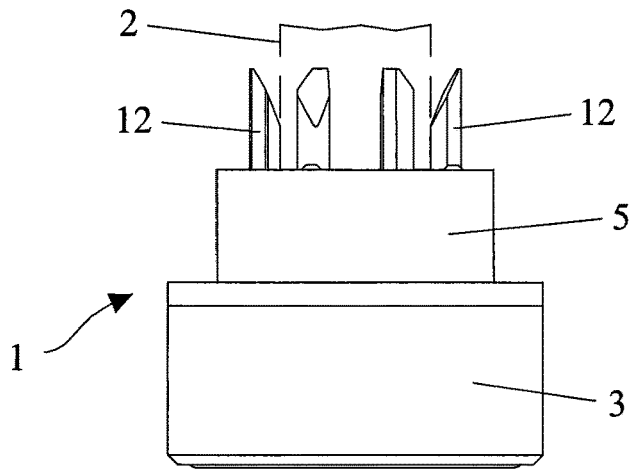
FIG. 1 shows a side view of the carrier device according to the present invention.
Figure 2:
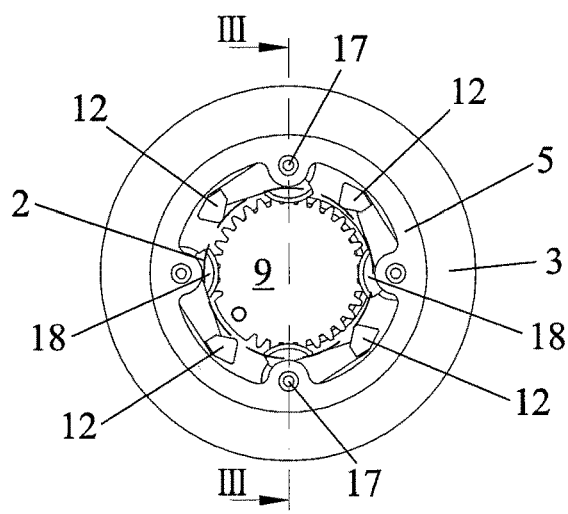
FIG. 2 shows a plan view from above of the carrier device in FIG. 1.

A carrier device 1 for a single container of biological products or single test tube 2 comprises a base 3 with a cavity 4, and a closing element 5 (FIGS. 1-4).

Base 3 has a central pin 6 with a cavity 7 in which there is accommodated an RFID transponder 8 capable of communicating data to a network of antennas distributed below the conveyor belt of the laboratory automation system so as to track the path of the carrier device 1, thus controlling the proper directing thereof along the system.

Base 3 is rotationally coupled to a toothed rotor 9, and further comprises four coupling holes 10, obtained in four cylinders 20 projecting upward and having vertical axis, in which pins 11 of four vertical gripping fingers 12 are inserted.

Each of said fingers 12 has, in turn, a gear 18 which engages a ring gear 21 of the toothed rotor 9, as well as pins 16 which engage coupling holes 17 of the closing element 5.

The toothed rotor 9 further comprises a hollow cylinder 22 which supports said ring gear 21 at the bottom and is adapted to rotationally engage on pin 6 of base 3.

Figure 3:
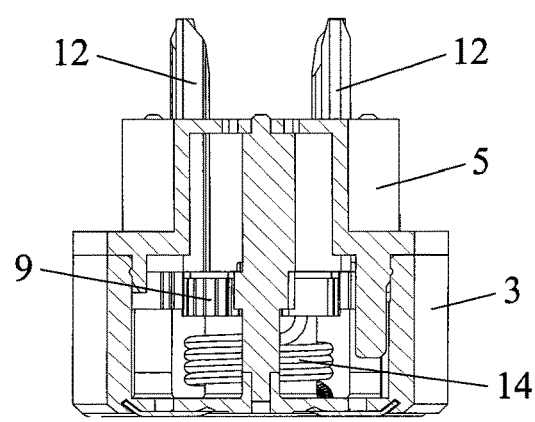
FIG. 3 shows a sectional view according to the line III-III in FIG. 2.
Figure 4:
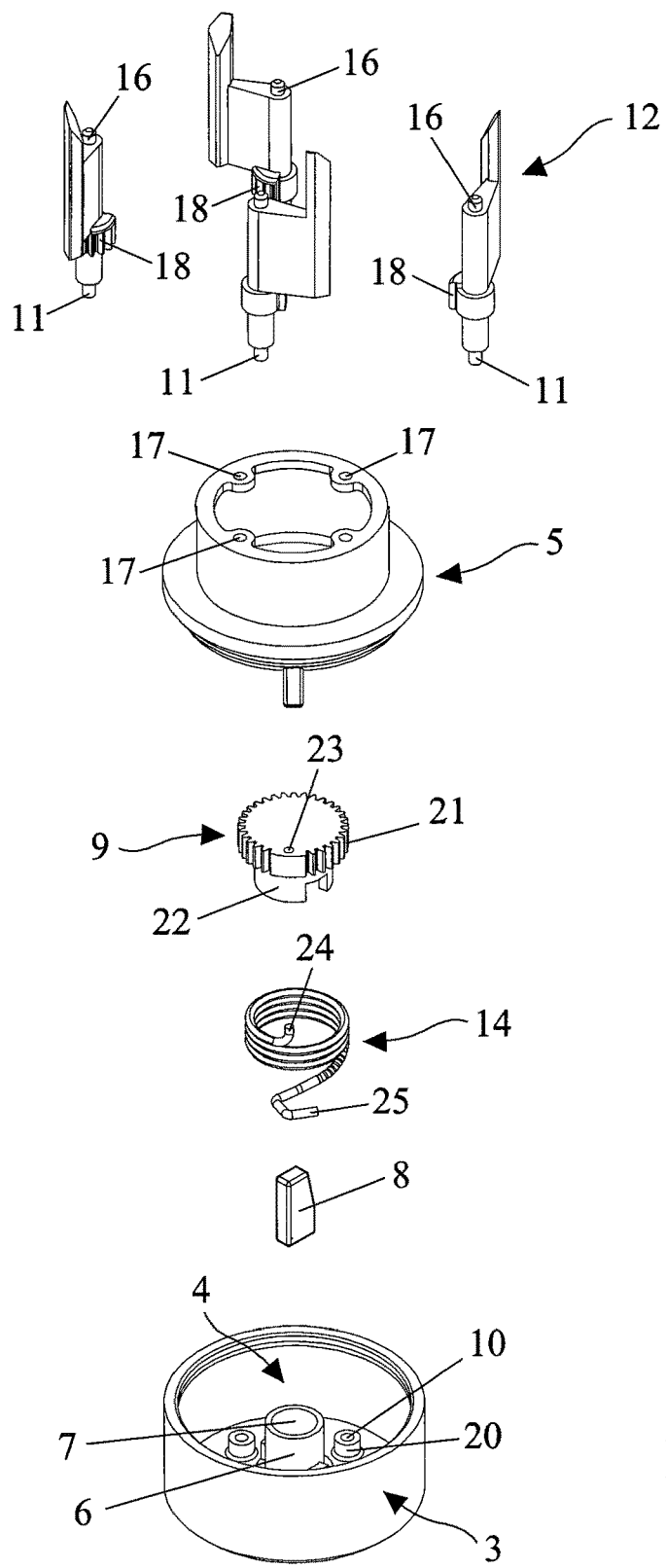
FIG. 4 shows an exploded view of the carrier device.

Said hollow cylinder 22 has a diameter which is smaller than the diameter of the ring gear 21 which therefore projects radially outward with respect to said hollow cylinder 22 (FIG. 3).

A spiral spring 14 is wound around the hollow cylinder 22 and is fixed to the toothed rotor 9 by means of an end 24 which is inserted from the bottom into a hole 23 of the ring gear 21.

A second hook-shaped end 25 is adapted to couple to one of the cylinders 20 of base 3. In essence, end 25 embraces one of the cylinders 20.

The spiral portion of spring 14 that embraces the hollow cylinder 22 has a radial size which is smaller than the diameter of the ring gear 21. Thereby, spring 14 maintains a radial size which is smaller than the one of the ring gear 21 also after assembly with the toothed rotor 9 (FIG. 3).

In essence, the difference in radial diameter between the ring gear 21 and the hollow cylinder 22 serves to create radial space for spring 14, which thus does not project with respect to the ring gear 21, thus keeping the assembly formed by spring 14 and by the toothed rotor 9 compact and not very cumbersome, with an optimal distribution of the gripping stresses of the fingers 12.

In a resting situation of the gripping fingers 12, that is when the carrier device 1 does not accommodate any test tube 2, each of the four fingers 12 rotates in anticlockwise direction about its pin 16, that is toward the middle of the toothed rotor 9, promoted by the action of spring 14 connected to rotor 9 itself, which ring gear 21 is, in turn, engaged with gear 18 of each of the fingers 12.

It is precisely the simultaneous engagement of the toothed rotor 9 with all the gears 18 of the gripping fingers 12 that ensures the suitable synchronization of the movement of all the fingers 12, and therefore a balance of the stress exerted inward by each of them.

When a test tube 2 is inserted into the carrier device 1 from above (FIGS. 1, 2), the sizes of the test tube 2 contribute to causing a rotation of the gripping fingers 12 in clockwise direction, that is outward, while the toothed rotor 9 rotates a few degrees in anticlockwise direction.

At the same time, spring 14 instead acts in the opposite direction by causing the inward rotation of the gripping fingers 12, and thereby the test tube 2 is conveniently held by the fingers 12.

The synchronism is manifested in the action exerted by each of the fingers 12 on the test tube 2 due to the gears 18 of the fingers 12, and therefore the stress applied to the test tube 2 is completely balanced both inward and outward, especially thanks to the single spring 14.

Furthermore, the grip is completely integral and ensures the test tube 2 is held also in case of any knocks it may be subjected to 2, and also that it is kept in perfectly vertical position when it is subjected to operations such as, for example, uncapping or capping.

The holding of the test tube 2 is ensured whatever its diameter, thus considering all types of test tube 2 normally in use in laboratory automation systems.

The presence of a single spring 14 with simple coupling points to rotor 9 and to base 3 allows easy and quick assembly of the carrier device 1.

The invention thus conceived is susceptible to numerous modifications and variations, all falling within the scope of the invention concept.

In practice, any materials and also shapes may be used, depending on the needs.

The invention claimed is:

1. A carrier device for a single container of biological products or single test tube, comprising:
   a base;
   a toothed rotor;
   four vertical gripping fingers;
   a closing element; and
   a spiral spring;
   wherein the base comprises a first cavity, a central pin with a second cavity in which an RFID transponder is accommodated, four coupling holes obtained in four cylinders projecting upward and having vertical axes,
   wherein the base is rotationally coupled to the toothed rotor,
   wherein the toothed rotor comprises a hollow cylinder and a ring gear which is the toothed portion of the toothed rotor, the hollow cylinder being at a bottom of the ring gear and being able to rotationally engage the central pin of the base,
   wherein each of said vertical gripping fingers comprises a gear which engages the ring gear of the toothed rotor, a first pin and a second pin,
   wherein the second pins of the four vertical gripping fingers are inserted in the four coupling holes of the base,
   wherein the closing element comprises coupling holes which engage the first pins of the vertical gripping fingers,
   wherein the hollow cylinder has a diameter which is smaller than the diameter of the ring gear which therefore projects radially outward with respect to said hollow cylinder,
   wherein the spiral spring comprises a first end and a second hook-shaped end,
   wherein the spiral spring wounds around the hollow cylinder and is fixed to the toothed rotor by the first end which is inserted from a bottom of the ring gear into a hole of the ring gear, the second hook-shaped end of the spiral spring coupling to one of the cylinders of the base,
   wherein the spiral spring has a radial size which is smaller than the diameter of the ring gear before and after the fixing of the spiral spring to the toothed rotor.

* * * * *